United States Patent
Lowenborg et al.

(10) Patent No.: US 9,737,481 B2
(45) Date of Patent: *Aug. 22, 2017

(54) SPRAY FOAM CORTICOSTEROID PRODUCT

(71) Applicant: Delcor Asset Corporation, Lake Forest, IL (US)

(72) Inventors: Michael V. Lowenborg, San Antonio, TX (US); Kuljit Bhatia, San Antonio, TX (US)

(73) Assignee: Delcor Assett Corporation, Lake Forest, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/015,612

(22) Filed: Feb. 4, 2016

(65) Prior Publication Data
US 2016/0220488 A1 Aug. 4, 2016

Related U.S. Application Data

(63) Continuation of application No. 14/596,867, filed on Jan. 14, 2015, now Pat. No. 9,265,727.

(51) Int. Cl.
| | | |
|---|---|---|
| *A61K 9/12* | (2006.01) | |
| *A61K 9/00* | (2006.01) | |
| *A61K 31/573* | (2006.01) | |
| *B65D 83/14* | (2006.01) | |
| *A61K 47/26* | (2006.01) | |
| *A61K 47/12* | (2006.01) | |
| *A61K 47/06* | (2006.01) | |
| *A61K 31/57* | (2006.01) | |
| *A47K 5/14* | (2006.01) | |
| *A61K 47/10* | (2017.01) | |
| *B65D 83/20* | (2006.01) | |

(52) U.S. Cl.
CPC ............ *A61K 9/122* (2013.01); *A47K 5/14* (2013.01); *A61K 9/0014* (2013.01); *A61K 9/124* (2013.01); *A61K 31/57* (2013.01); *A61K 31/573* (2013.01); *A61K 47/06* (2013.01); *A61K 47/10* (2013.01); *A61K 47/12* (2013.01); *A61K 47/26* (2013.01); *B65D 83/207* (2013.01); *B65D 83/752* (2013.01); *B65D 83/20* (2013.01)

(58) Field of Classification Search
None
See application file for complete search history.

(56) References Cited

U.S. PATENT DOCUMENTS

| | | | |
|---|---|---|---|
| 6,126,920 A | 10/2000 | Jones et al. | |
| 6,730,288 B1 | 5/2004 | Abram | |
| 7,029,659 B2 | 4/2006 | Abram | |
| 8,460,641 B2 | 6/2013 | Larm et al. | |
| 9,119,781 B2 | 9/2015 | Lind et al. | |
| 9,265,727 B1* | 2/2016 | Lowenborg | A61K 9/122 |
| 9,345,666 B1* | 5/2016 | Lowenborg | A61K 9/122 |
| 2004/0151671 A1* | 8/2004 | Abram | A61K 8/046 424/45 |
| 2005/0031547 A1* | 2/2005 | Tamarkin | A61K 8/046 424/45 |
| 2011/0256070 A1* | 10/2011 | Martin | A61K 9/0019 424/45 |

FOREIGN PATENT DOCUMENTS

| | | |
|---|---|---|
| AU | 463216 | 11/1973 |
| WO | WO 85/01876 A1 | 5/1985 |

OTHER PUBLICATIONS

Bierman. J Am Med Assn 106(14):1158/1162 (1936.
Commonly Used Emulsifiers and their HLB Values, University of North Carolina Eshelman School of Pharmacy, 1996-2014.
Sunita, IRJP (2012), pp. 68-75, vol. 3, Issue 9.

* cited by examiner

*Primary Examiner* — Richard Schnizer
*Assistant Examiner* — Katherine Peebles

(57) ABSTRACT

A foamable pharmaceutical composition and a method of treating corticosteroid-responsive dermatoses of the skin are disclosed. The foamable pharmaceutical composition comprises a corticosteroid compound as an active ingredient; a quick-break foaming agent including an aliphatic alcohol, water, a fatty alcohol and a surface active agent; a buffering agent; and a propellant. The foamable composition is disposed within a pressurizable container that comprises an aerosol valve assembly including a dip tube communicating with a valve orifice through which the foamable composition is dispensed and an actuator to start and stop dispensation. The valve assembly dispenses a conically-shaped spray at a rate of about 2 to about 0.3 g/sec and provides a foam having a density of about 0.12 to about 0.25 when sprayed at a distance of about 5 to about 10 cm from the valve orifice onto a glass surface that is at ambient room temperature.

18 Claims, 6 Drawing Sheets

SPRAY FOAM CORTICOSTEROID PRODUCT

TECHNICAL FIELD

The present invention contemplates an improved corticosteroid product that provides a sprayed foam-containing corticosteroid for the topical application to the skin of a subject.

BACKGROUND OF THE INVENTION

Corticosteroids, particularly in the form of the ester derivative compounds, are used, inter alia, in the treatment of skin diseases in humans, such as eczema, infantile eczema, atopic dermatitis, dermatitis herpetiformis, contact dermatitis, seborrhoeic dermatitis, neurodermatitis, psoriasis and intertrigo. Formulations containing such active substances have conventionally been applied to the skin site in the form of alcoholic solutions, lotions or creams.

However, lotions and creams can be too viscous to permit efficient penetration of the active substance to the epidermis, and solutions have a tendency to evaporate before penetrating the epidermis. In addition, conventional cream bases can be irritating to the skin, particularly over the often long exposure that is required, and the fluidity of lotions often makes the physical application difficult to control. Moreover, it is necessary to rub such formulations into the target site to improve the penetration of the active substance into the epidermis, an action that itself can produce irritation.

There has therefore been a very real need in the treatment of skin disorders requiring treatment with corticosteroids for improved formulations which target the most effective corticosteroid to the skin site with improved delivery of active, substance with decreased inconvenience and irritation, and increased ease of use for the patient. One such improvement has been in the product sold under the name Olux® (clobetasol propionate) Foam 0.05%. Olux® Foam 0.05% contains clobetasol propionate in a thermolabile hydroethanolic foam vehicle pressurized by a hydrocarbon (propane/butane) propellant. This product is described and claimed in U.S. Pat. No. 6,126,920.

The product label, inter alia, instructs morning and evening applications that can be effected by inverting the pressurized container and dispensing a small amount of the hair mousse-like foam (up to a maximum of a golf-ball-size dollop or one and a half capfuls) into the cap of the can, onto a saucer or other cool surface, or to the lesion, taking care to avoid contact with the eyes. Dispensing directly onto hands is not recommended (unless the hands are the affected area), as the foam will begin to melt immediately upon contact with warm skin. Small amounts of the foam are suggested to be picked up with fingertips and gently massaged into affected area until the foam disappears.

U.S. Pat. Nos. 7,029,659 and 6,730,288 both to Abram that are titled "Mousse Composition" and U.S. Pat. No. 8,460,641 to Larm et al. describe aerosol foaming compositions for dermatological use. The Abram compositions are described as a mousse, whereas a Larm et al. composition is described as an oil in water microemulsion or sub-micron emulsion that can be dispensed "as an aerosol foam or mousse" (col. 16, lines 35-36). A composition of each patent is said to contain at least one occlusive agent such as one or both of petrolatum and mineral oil, one or more lipophilic surfactants, water, at least one hydrophilic surfactant, a non-surfactant water-soluble amphiphilic agent such as a diol or polyol, a pharmaceutically active ingredient that is poorly water-soluble such as betamethasone valerate or clobetasol propionate, and a propellant. A composition of the three patents can also contain an organic solvent.

Each of these patents is listed in the FDA "Orange Book" in conjunction with a product called "Olux-E®". This product is to be indicated for the treatment of inflammatory and pruritic manifestations of corticosteroid-responsive dermatoses in patients 12 years and older. The active ingredient is 0.05% clobetasol propionate. The instructions for use of Olux-E® indicate that the aerosol container be shaken, and inverted to dispense the foam into the palm of one's hand. The dispensed foam is then to be applied to the affected area in a thin layer and the foam gently rubbed into the affected area until it disappears into the skin.

The Olux® (clobetasol propionate) Foam 0.05% product is a particularly efficacious product, but is somewhat inconvenient and cumbersome to use because of the requirement for container inversion to dispense the foam and the related difficulties in dispensing the foam into the container cap, the stiffness of the dispensed foam that can require excessive rubbing and irritation on use, and the wastage involved in dispensing the foam into the product cap and scooping out the dispensed foam with the user's fingers to apply it to the affected area. The present invention provides improvements in these areas, while maintaining the desired pharmaceutical results.

BRIEF SUMMARY OF THE INVENTION

In one aspect, the present invention provides a foamable pharmaceutical composition comprising a corticosteroid active substance, preferably clobetasol propionate or betamethasone valerate, a quick-break foaming agent, a propellant and a buffering agent. More specifically, a contemplated foamable pharmaceutical product comprises a foamable pharmaceutical composition that contains an effective amount of a corticosteroid compound that has utility in the topical treatment of skin disorders as an active ingredient; a quick-break foaming agent that comprises (a) a straight or branched chain $C_1$-$C_4$ aliphatic alcohol, (b) water, (c) a fatty alcohol and (d) a surface active agent. A buffering agent present in an amount sufficient to provide a pH value of about 3.0 to about 6.0 and a propellant are also present. The foamable pharmaceutical composition is disposed in a sealed pressurizable container typically at an internal pressure of about 40 to about 80 psi. The container comprises an aerosol valve assembly that includes a dip tube in communication with a valve orifice through which the foamable pharmaceutical composition can be dispensed and an actuator to start and stop foam dispensation. The valve assembly on being actuated dispenses a substantially conically-shaped spray having an apex adjacent the valve orifice. The spray is dispensed at a rate of about 0.3 to about 2 g/sec and provides a foam having an initial density of about 0.12 to about 0.25 g/mL when sprayed at a distance of about 5 to about 10 cm (about 2 to about 4 inches) from the valve orifice onto a glass or plastic surface that is at ambient room temperature, and preferably an initial density of about 0.12 to about 0.2.

The phrase "initial density" is used herein to refer to the foam density measured on spraying the composition on to a glass or plastic surface such as that of a glass beaker or into a plastic syringe at ambient room temperature (the beaker or syringe) rather than on spraying on to the skin because of the ease of the former measurement and the difficulty of the latter measurement due to the rapid collapse of the foam on contact with the skin. The initial density as defined herein is believed to be a reasonable approximation of the density of the foam when it is first applied to the skin, and is used herein to refer to both application of the foam to a glass surface and to when the foam is first applied to a skin surface before it begins to break down. A method of carrying out this measurement is discussed hereinafter.

A method of treating corticosteroid-responsive dermatoses of the scalp or mild to moderate plaque-type psoriasis of the scalp or non-scalp region of the skin is also contemplated. In that method, one sprays directly on to a skin area to be treated or into a hand for further application a foamable pharmaceutical composition that comprises (1) a corticosteroid compound that has utility in the topical treatment of skin disorders such as clobetasol propionate or betamethasone valerate as an active ingredient, (2) a quick-break foaming agent that comprises (a) a straight or branched chain $C_1$-$C_4$ aliphatic alcohol present at about 40 to about 90% w/w composition, (b) water present at about 9 to about 40% w/w, (c) a fatty alcohol present at about 0.5 to about 10% w/w, and (d) a nonionic surface active agent having an HLB value of about 13 to about 17 present at about 0.1 to about 50% w/w, and (3) a propellant. The spray emanates in a substantially conical shape at a dispensing rate of about 0.3 to about 2 g/sec and provides a foam having an initial density of about 0.12 to about 0.25 g/mL when sprayed at a distance of about 5 to about 10 cm from the valve orifice onto a glass or plastic surface that is at ambient room temperature. The foamable pharmaceutical composition is disposed in a pressurizable container typically at an internal pressure of about 40 to about 80 psi that comprises an aerosol valve assembly that includes a dip tube extending into the foamable pharmaceutical composition from the aerosol valve assembly. The dip tube is in communication with a valve orifice through which the foamable pharmaceutical composition can be dispensed and an actuator to start and stop dispensation. The sprayed foamable pharmaceutical composition is dispersed on the scalp or non-scalp region of the skin to be treated or by the hand. The sprayed foamable pharmaceutical composition is maintained on the scalp or non-scalp region of the skin to be treated until the composition has been sorbed (absorbed, adsorbed or otherwise taken up) by the skin and can be spread over the skin as desired.

BRIEF DESCRIPTION OF THE DRAWINGS

In the drawings forming a portion of this disclosure

Figure 1:
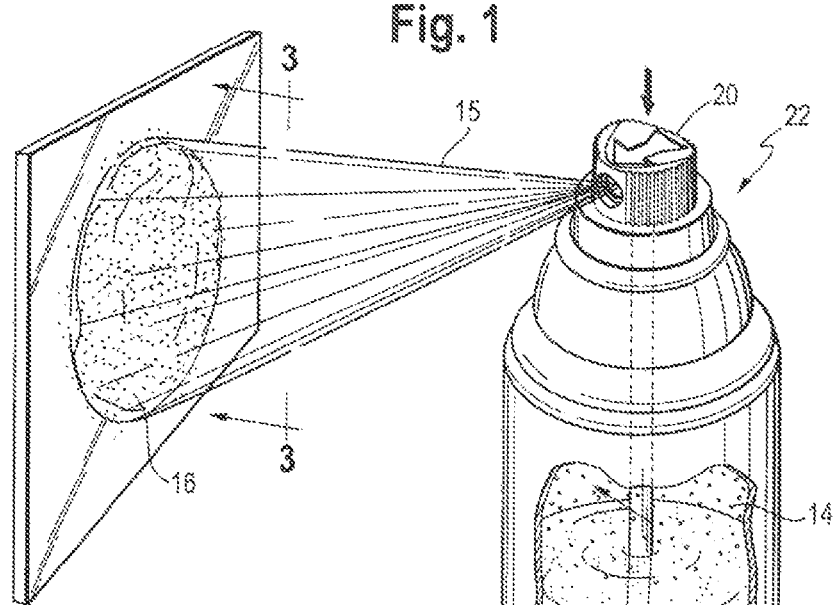
FIG. 1 is a partial cut-away view of an illustrative container and foamable pharmaceutical composition of the invention being dispensed on to a glass surface.

The present invention has a number of benefits and advantages, several of which are discussed below:

One benefit is that the container need not be inverted to dispense the contents, thereby providing better control of dispensed foam, and improved patient compliance by avoiding the need to invert the prior container to dispense a dollop of foam, which can be cumbersome to patients.

An advantage of the invention is that the foam need not be rubbed as much as for the prior product, so that the affected skin is typically less irritated.

Another benefit is that there is less product wastage because the foam can be dispensed on to the affected area and need not be scooped out of the container top.

Another advantage of the inventions is that the smaller and uniform foam bubble size provide more manageable dispensing and use of the product.

Still further benefits and advantages will be apparent to the skilled worker from the disclosure that follows.

DETAILED DESCRIPTION OF THE INVENTION

A pharmaceutical product is contemplated that contains an effective amount of a corticosteroid compound that has utility in the topical treatment of skin disorders, preferably clobetasol propionate or betamethasone valerate, that is dissolved or dispersed in a foamable pharmaceutical composition. A quick-break (quick-collapsing) foaming agent is used in the present invention. Suitable quick-break foaming agents in the present invention are those, for example, described in Australian Patent No. 463216, and International Patent Application WO 85/01876, and U.S. Pat. No. 6,126, 920. A contemplated quick-break foam collapses into a liquid in less than about one minute when a 2 gram dosage is sprayed onto live human skin.

A contemplated quick-breaking foaming agent comprises a $C_1$-$C_4$ aliphatic alcohol, water, a fatty alcohol and a surface active agent. Particularly preferred is a quick-break foaming agent having the following composition:

(a) a straight or branched chain $C_1$-$C_4$ aliphatic alcohol, preferably in amounts of about 40 to about 90% w/w composition, more preferably about 55 to about 70% w/w, especially about 57 to about 62% w/w;

(b) water, preferably in amounts of about 9 to about 40% w/w, and more preferably about 25 to about 40% w/w;

(c) at least one fatty alcohol, preferably in an amount of about 0.5 to about 10% w/w; more preferably at about 1 to about 3% w/w; and (d) a surface active agent that is preferably nonionic, and preferably has an HLB (hydrophilic-lipophilic balance) value of about 13 to about 17 (as emulsifier), typically in amounts of about 0.1 to about 50% w/w, preferably at about 0.2 to about 10% w/w, and more preferably at about 0.3 to about 5% w/w.

A contemplated aliphatic alcohol is preferably a straight or branched chain $C_1$-$C_4$ alcohol such as methyl alcohol, ethyl alcohol (ethanol), n-propanol, isopropyl alcohol, iso-butyl alcohol, sec-butyl alcohol and t-butyl alcohol, and mixtures of two or more thereof. Ethanol has been found to be particularly preferred.

In the quick-break foaming agent, the fatty alcohol is preferably a $C_{12}$-$C_{18}$ fatty alcohol and can be, for example, oleyl, stearyl, lauryl, myristyl and palmityl (cetyl) alcohols and mixtures of two or more thereof as are found in natural and synthetic $C_{12}$-$C_{18}$ fatty alcohols such as coco and tallow fatty alcohols.

Mixtures of cetyl alcohol and a stearyl alcohol such as octadecan-1-ol have been found to be particularly preferred; the ratio between those two components can be adjusted to maintain foam viscosity throughout the broadest possible temperature range. A weight ratio of about 3:1 to about 1:1 (cetyl:stearyl alcohols) is preferred, and a ratio of about 5:2 to about 2:1 is more preferred. In this situation, the stearyl alcohol maintains the viscosity at temperatures above about 20° C., whereas cetyl alcohol maintains the viscosity below about 20° C.

A surface active agent (surfactant) utilized in the quick-break foaming agent is preferably a chemical compound that is free of ionic charge at a pH value of about 5 to about 9 (nonionic) and preferably has an HLB (hydrophilic-lipophilic balance) value of about 13 to about 17, and more preferably about 14 to about 16. Illustrative surface active agents are preferably chosen from (a) ethoxylated sorbitan $C_{12}$-$C_{18}$ esters (laurate, myristate, stearate, palmitate, or oleate), (b) nonyl phenol ethoxylates and (c) $C_{12}$-$C_{18}$ fatty alcohol ethoxylates, and mixtures of two or more thereof. The surface active agent enhances the fatty alcohol solubility in the system and enhances foam formation.

Illustratively, ethoxylated sorbitan $C_{12}$-$C_{18}$ esters include for example, polysorbate 60 (a mixture of partial stearic acid esters of sorbitol and its anhydrides copolymerized with approximately 20 moles of ethylene oxide for each mole of sorbitol and its anhydrides) that has been found to be particularly preferred. Other similar molecules include polysorbate 40, which is a palmitate ester with about 20 moles of polymerized ethylene oxide per mole, and polysorbate 20, which is a laurate ester also with an average of about 20 moles of polymerized ethylene oxide per mole. These surfactants have the following HLB values: polysorbate 60 HLB 14.9; polysorbate 40 HLB 15.6; polysorbate 20 HLB 16.7.

Illustrative nonyl phenol ethoxylates include those materials referred to in the surfactant industry as nonoxynol-9.0, nonoxynol-10, nonoxynol-11, nonoxynol-13, nonoxynol-15, nonoxynol-18, nonoxynol-20 and nonoxynol-30. These surfactants have HLB values of 12.98, 13.87, 14.57, 15.00, 15.66, 16.00, 17.14, respectively, and contain an average of 9, 10, 11, 13, 15, 18, 20 and 30 moles of ethylene oxide per molecule, respectively.

Illustrative $C_{12}$-$C_{18}$ fatty alcohol ethoxylates are often referred to in the surfactant industry by the conventional stem name (prefix) of the fatty alcohol such as laur ($C_{12}$), cet ($C_{16}$), stear ($C_{18}$), ole ($C_{18}$, one double bond) or cetar (mixed $C_{16}$ and $C_{18}$) followed by the letters "-eth" (or "th" for oleth) and then a number that indicates the average number of moles of ethylene oxide per mole of surfactant. Illustrative $C_{12}$-$C_{18}$ fatty alcohol ethoxylates so named and exhibiting a HLB value of about 13 to about 17 include oleth-10 (HLB 13.0), steareth-20 (HLB 15.3), oleth-20 (HLB 15.3), cetareth-20 (HLB 15.5), ceteth-20 (HLB 15.7), and steareth-30 (HLB 16.7).

Ethoxylated paraffinic alcohols (synthetic) that contain both odd- and even-numbered carbon chains utilize the number of carbon atoms in the chains of the mixture followed by the word "pareth" and then a number for the average number of ethylene oxide units per molecule. For example, C12-13 pareth-7 is a mixture of twelve and thirteen carbon alcohols, each having an average of 7 moles of added ethylene oxide per molecule and is available from Stepan Co., Northfield, Ill., USA under the designation BIO-SOFT® N23-6.5.

The names polysorbate followed by a number, nonyl phenol ethoxylates such as "nonoxynol-9", and the several forms of ethoxylated alcohols whose names include the "-eth" suffix are the formal names given to those compounds in the *International Cosmetic Ingredient Dictionary and Handbook*, eighth ed., Wenninger et al. eds., The Cosmetic, Toiletry, and Fragrance Association, Washington, D.C. (2000).

The propellant used can be chosen from conventional aerosol propellants. Thus, one can select the propellant from propane, butane, dichlorodifluoromethane, dichlorotetrafluoro ethane, octafluoro cyclobutane, and mixtures of two or more thereof. It is preferred to select a propellant most compatible with the entire system.

It is particularly preferred that the propellant be present in amounts preferably of about 3 to about 30% w/w, more preferably about 3 to about 10% w/w, especially about 3 to about 5% w/w. The maximum level of propellant is typically determined as the amount miscible with the utilized water/aliphatic alcohol ratio. In addition to acting as a propellant, the propellant also acts as a solvent for the fatty alcohols and active substances in the aqueous/alcoholic system.

A fragrance is also preferably present. Illustrative fragrances include extracts of natural materials such as terpenes and terpenoids like menthol, camphor, limonene, lavender oil, mint oil, peppermint oil, lemon oil, spearmint oil and the like. Menthol is a particularly preferred fragrance. A fragrance is typically present at about 0.02 to about 0.1% w/w, and more preferably at about 0.05 to about 0.08% w/w.

Other additives can also be used. Thus, it is preferred to add a humectant to reduce the drying effects of the aqueous aliphatic alcohol. Such a humectant can preferably be present in an amount of about 0.1 to about 10.0% w/w, more preferably about 0.5 to about 3.0% w/w. It is particularly preferred that the humectant be propylene glycol, but other humectants such as glycerine, panthenol and sorbitol can be used.

A foamable pharmaceutical composition of the present invention contains and is used to deliver a corticosteroid compound or other medicament that has utility in the topical treatment of skin disorders. Thus, for example, a pharmaceutical composition of the present invention can be used to deliver one or a mixture of the following topically-effective corticosteroids: alclometasone dipropionate, fluclorolone acetonide, amcinonide, fluocinolone acetonide, beclamethasone dipropionate, fluocinonide, betamethasone benzoate, fluocortin butyl, betamethasone dipropionate, fluocortolone preparations, betamethasone valerate, fluprednidene acetate, budesonide, flurandrenolone, clobetasol propionate, halcinonide, clobetasone butyrate, hydrocortisone desonide, hydrocortisone acetate, desoxymethasone, hydrocortisone butyrate, diflorasone diacetate, methylprednisolone acetate, diflucortolone valerate, mometasone furoate, flumethasone pivalate, triamcinolone acetonide, and pharmacologically effective mixtures thereof.

A composition according to the invention is especially advantageous for the topical administration to the skin of human subjects of clobetasol or betamethasone and their derivatives such as clobetasol propionate or betamethasone benzoate, betamethasone dipropionate, or betamethasone valerate. It is particularly preferred to use clobetasol propionate or betamethasone valerate, especially in the treatment of psoriasis.

The corticosteroid active substance is preferably present in an amount of about 0.01 to about 1.0% w/w, and more preferably about 0.05 to about 0.2% w/w.

To ensure stability of the active isomer of the corticosteroid in the composition and thus to ensure delivery of the most active isomer to the epidermis, the composition is buffered by including a suitable buffering agent. Suitable buffering agents are acetic acid/sodium acetate, citric acid/sodium citrate and phosphoric acid/sodium phosphate, and it is desirable generally to buffer the composition to about pH 3 to about pH 6, preferably about pH 4 to about pH 5. The buffering agent is preferably present in an amount of about 0.01 to about 1.0% w/w, and more preferably about 0.05 to about 0.2% w/w.

It is particularly preferred to use a citrate buffer system, more preferably citric acid/potassium citrate, to buffer the composition to pH 4.5, when clobetasol propionate or betamethasone valerate is used as the active substance. For betamethasone valerate, citrate buffering stabilizes the more active 17-valerate ester over the less active 21-valerate ester in the complex composition and ensures that the most effective form of the active substance is efficiently delivered to the epidermis.

Preparation of the composition can be effected by conventional means so as to produce a homogeneous solution of fatty alcohol(s) in an aliphatic alcohol/water base. The relative proportions of the fatty alcohol(s), water/aliphatic alcohol and propellant are conveniently controlled according to conventional means so as to provide a homogeneous clear solution and so as to permit the formation of a suitable quick-break foam.

Typically, the fatty alcohol(s), surface active agent, aliphatic alcohol, fragrance (when present) and humectant (if present) are preferably mixed together with the corticosteroid active substance to produce an "Alcohol Phase". An "Aqueous Phase" is preferably produced by mixing the buffering agent and water. These phases are then mixed, preferably in the final container, in the required amounts. The valve assembly is added, the vessel containing the valve assembly and all of the ingredients except the propellant is sealed. The propellant is then added to the sealed vessel under pressure to produce the composition according to the invention.

In the case of betamethasone valerate or clobetasol propionate as an active ingredient, it is particularly preferred to use a composition comprising cetyl alcohol and octadecan-1-ol as fatty alcohols, together with polysorbate 60 surface active agent, with purified water and ethanol as the aliphatic alcohol. The system is preferably buffered with citric acid/potassium citrate and the propellant is preferably butane/propane. It is generally preferred to choose the proportion of the components to achieve a fixed pressure in the container of about 40 to about 80 psi, and more preferably about 50 to about 70 psi.

The composition of the present invention is contained in and dispensed from a container (vessel) capable of withstanding the pressure of the propellant gas and having an appropriate valve/nozzle for dispensing the composition under pressure. If the container is made of a metal material likely to suffer corrosion under the action of the composition, the composition can include a corrosion inhibitor as an additive.

Thus, the presence of a corrosion inhibitor can be necessary if the container is made of tin plate. Suitable corrosion inhibitors include organic acid salts, preferably chosen from sorbic acid, benzoic acid, sodium benzoate and potassium sorbate. If used, the corrosion inhibitor can be present in amounts of about 0.1 to about 15% w/w, more preferably about 0.1 to about 3% w/w. In the present invention, aluminum cans are preferred as containers, particularly when utilizing the above-mentioned composition for clobetasol propionate or betamethasone valerate as the corticosteroid active substance; in this case there is no corrosion problem and there is no need for the inclusion of a corrosion inhibiting agent.

In use, foamable composition is dispensed from the orifice of the valve usually located in the actuator in a substantially conically-shaped spray. The apex of the cone shape may not be visible, providing a frustoconical shape rather than a complete cone shape so that the spray is substantially conically-shaped. The composition forms a foam on being dispensed due to the gasification/evaporation of the dissolved or dispersed propellant.

The spray is typically dispensed at a rate of about 0.3 to about 2 g/sec, and more preferably at a rate of about 0.5 to about 1 g/sec sprayed on to a glass surface, preferably the surface of a pane of glass, at ambient room temperature from a distance of about 5 to about 10 cm from the valve orifice was measured to be about 0.1 to about 0.2 g/mL. A usual dosage amount is about 2 grams. A foam having an initial density of about 0.12 to about 0.25 g/mL is produced when the composition is sprayed at a distance of about 5 to about 10 cm (about 2 to about 4 inches) from the valve orifice onto a glass or preferably plastic surface that is at ambient room temperature. Preferably, the foam has an initial density of about 0.12 to about 0.2.

FIG. 1 in a partial cut-away view shows a contemplated foamable composition 10 disposed within its sealed pressurizable container 12, along with gaseous propellant 14. Dissolved propellant cannot be separately seen and is part of the foamable composition 10. Also shown in part are the dip tube 18 and the actuator 20 that are part of the aerosol valve assembly 22.

FIG. 1 also illustrates dispensing of a contemplated foamable composition 10 in its substantially conical spray pattern 15 on to an exemplary planar glass surface used to show the foam 16 that results from that dispensing.

Figure 2:
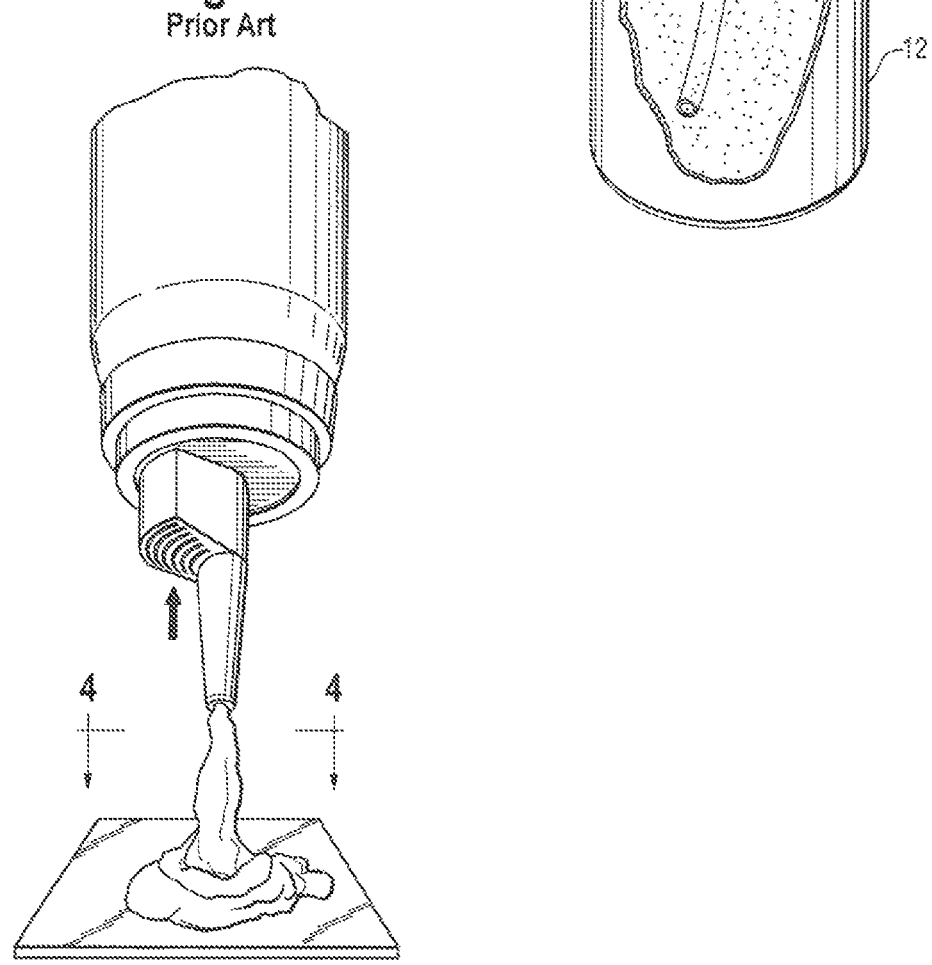
FIG. 2 illustrates the dispensing of the prior art Olux® (clobetasol propionate) Foam 0.05% product on to a planar glass surface.

FIG. 2 illustrates the dispenser shape and method and result of dispensing the prior art Olux® (clobetasol propionate) Foam 0.05% product as directed by the product label instructions.

Figure 3:
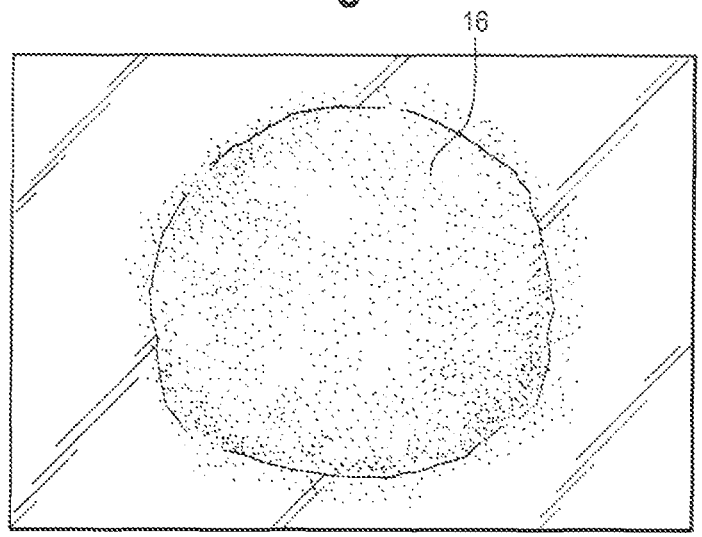
FIG. 3 is a top plan view taken along line 3-3 of FIG. 1 illustrates the general appearance of a contemplated foamable pharmaceutical composition when dispensed on to a planar glass surface.
Figure 4:
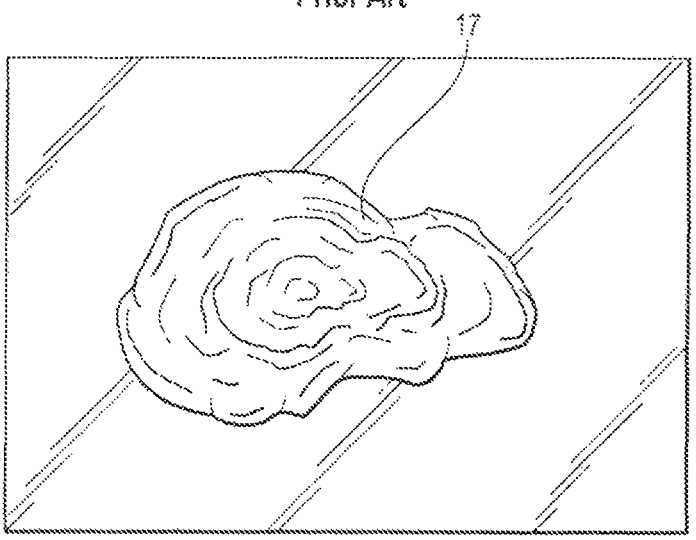
FIG. 4 is a top plan view taken along line 4-4 of FIG. 2 illustrates the general appearance of a the prior art Olux® (clobetasol propionate) Foam 0.05% product when dispensed on to a planar glass surface on following the product label instructions.

FIG. 3 shows atop plan view of the foam 16 dispensed from a contemplated pharmaceutical product comprised of a foamable pharmaceutical composition and pressurizable container. FIG. 4 shows a similar top plan view of the foam dollup 17 dispensed by the prior art Olux® (clobetasol propionate) Foam 0.05% product.

Figure 5:
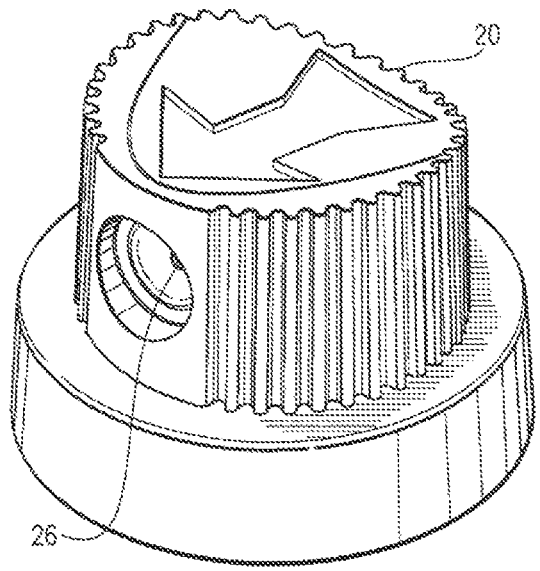
FIG. 5 is an elevation view of an actuator that is part of the valve assembly useful in a contemplated pharmaceutical product.
Figure 6:
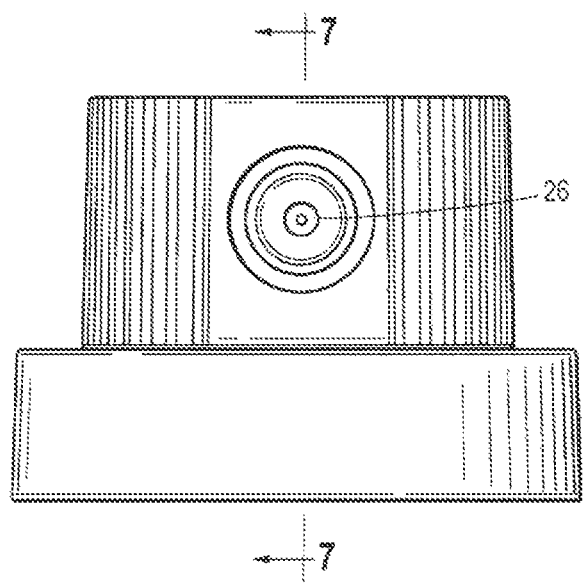
FIG. 6 is another elevation view of an actuator as in FIG. 5.
Figure 7:
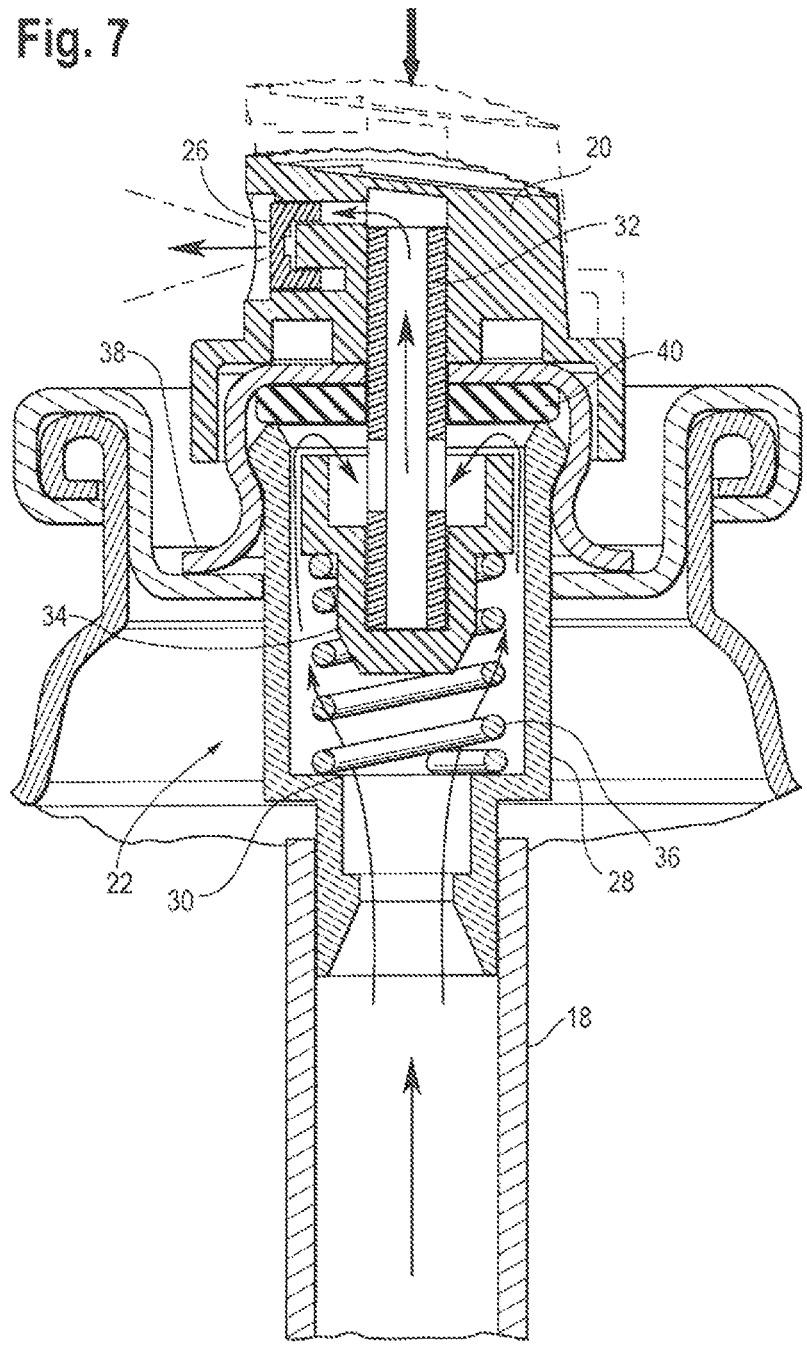
FIG. 7 is a cross-sectional view taken along line 7-7 of FIG. 6 in which the actuator is in place as a portion of the valve assembly of a pressurizable container and extending through a portion of the container in which the direction of flow of the foamable composition is shown by the dark arrows after the actuator is depressed from its closed position as shown by the dashed line and open arrow.

FIGS. 5 and 6 show views of an actuator 20 that is a portion of the valve assembly 22. The actuator includes (defines) an orifice 26 through which the foamable composition flows on dispensing and that communicates to the contents of the container via the valve housing 28 that connects to the dip tube 18 extending into the foamable composition 10. The valve assembly 22 also includes a stem 32 on which the actuator 20 is mounted and whose lower surface is contoured as a spring cup 34 to retain one terminus of a spring 36 with the other terminus of the spring constrained by the inner lower surface 30 of the valve housing 28. The valve assembly 22 is maintained and sealed within the valve housing by a valve mounting cup 38 and gasket 40.

Contrary to the instructions for use provided with Olux® (clobetasol propionate) Foam 0.05% product, a contemplated composition is sprayed onto the hand or the affected skin area, producing a thin build-up of foam that begins to break or collapse into a liquid almost immediately upon contacting human skin at a usual skin temperature of about 35° C. [about 33.5 to about 36.9° C.; Bierman, *JAMA* 1936 106(14):1158-1162]. Thus, when sprayed from a distance of about 5 to about 10 cm, 2 grams of the foam forms a circular deposit about 8 cm in diameter and about 1.5 to about 4 mm thick on a flat surface such as a glass plate, which glass plate is at ambient room temperature. Using the Olux® (clobetasol propionate) Foam 0.05% product that is designed to be dispensed as a thick mousse-like foam with the dispensing orifice in a downward position as shown on the label, and following the label instructions, the user obtains a 2 gram golf ball-sized dollop in the cap of the container that is then transferred to the skin.

Comparing the use of the Olux® (clobetasol propionate) Foam 0.05% product to an embodiment of the foamable pharmaceutical product of the invention, the Olux® (clobetasol propionate) Foam 0.05% product is inverted, discharged into its cap and then applied to the skin with the user's fingers, whereas the contents of a spray container disclosed herein can be sprayed directly on to the skin area to be treated and spread with one's fingers. A composition can also be sprayed into a hand for hand application to the skin area to be treated.

Figure 8:
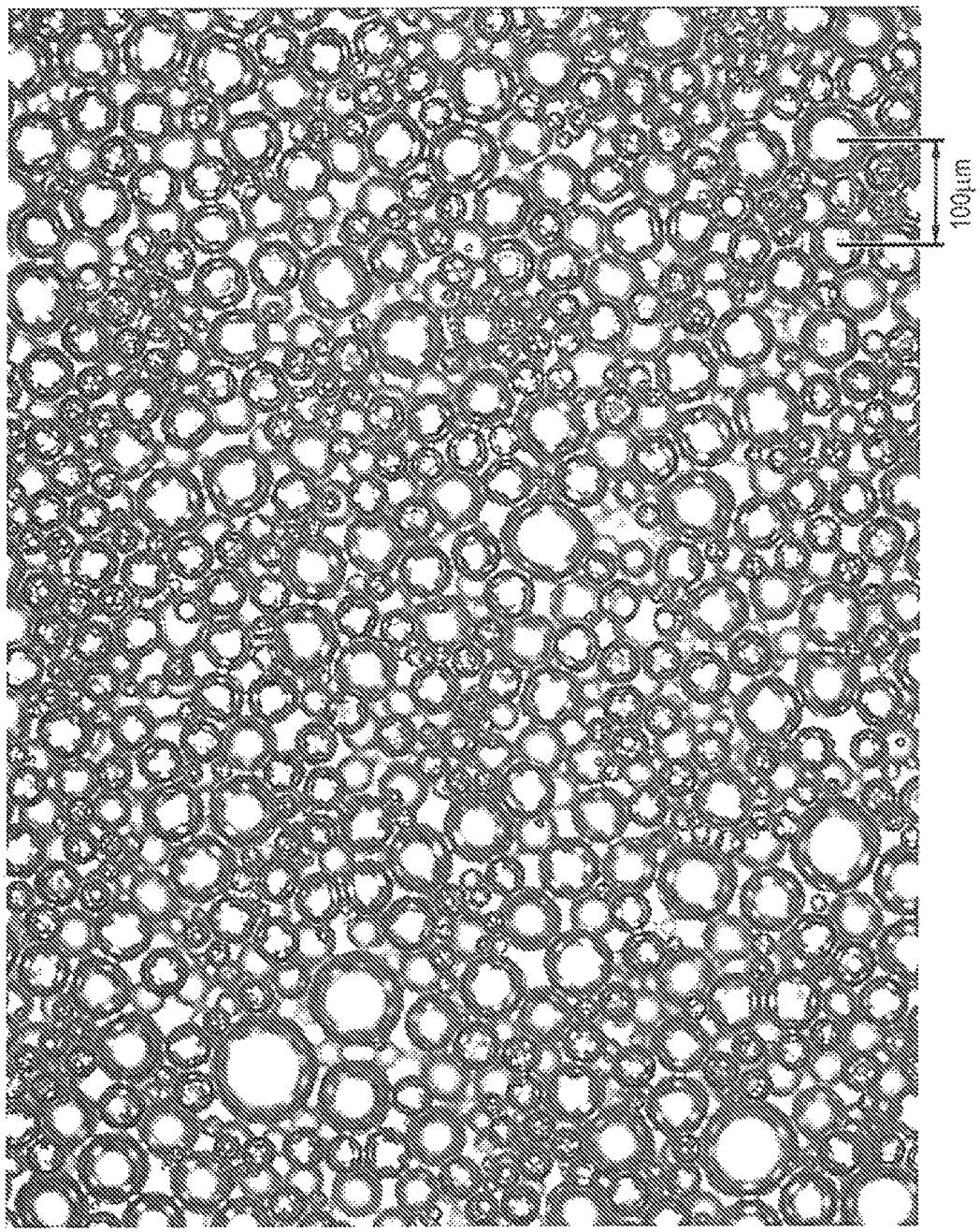
FIG. 8 is a photomicrograph of the foam produced by foamable pharmaceutical composition of the present invention that was dispensed on to a glass slide, covered and photographed at 100× magnification.
Figure 9:
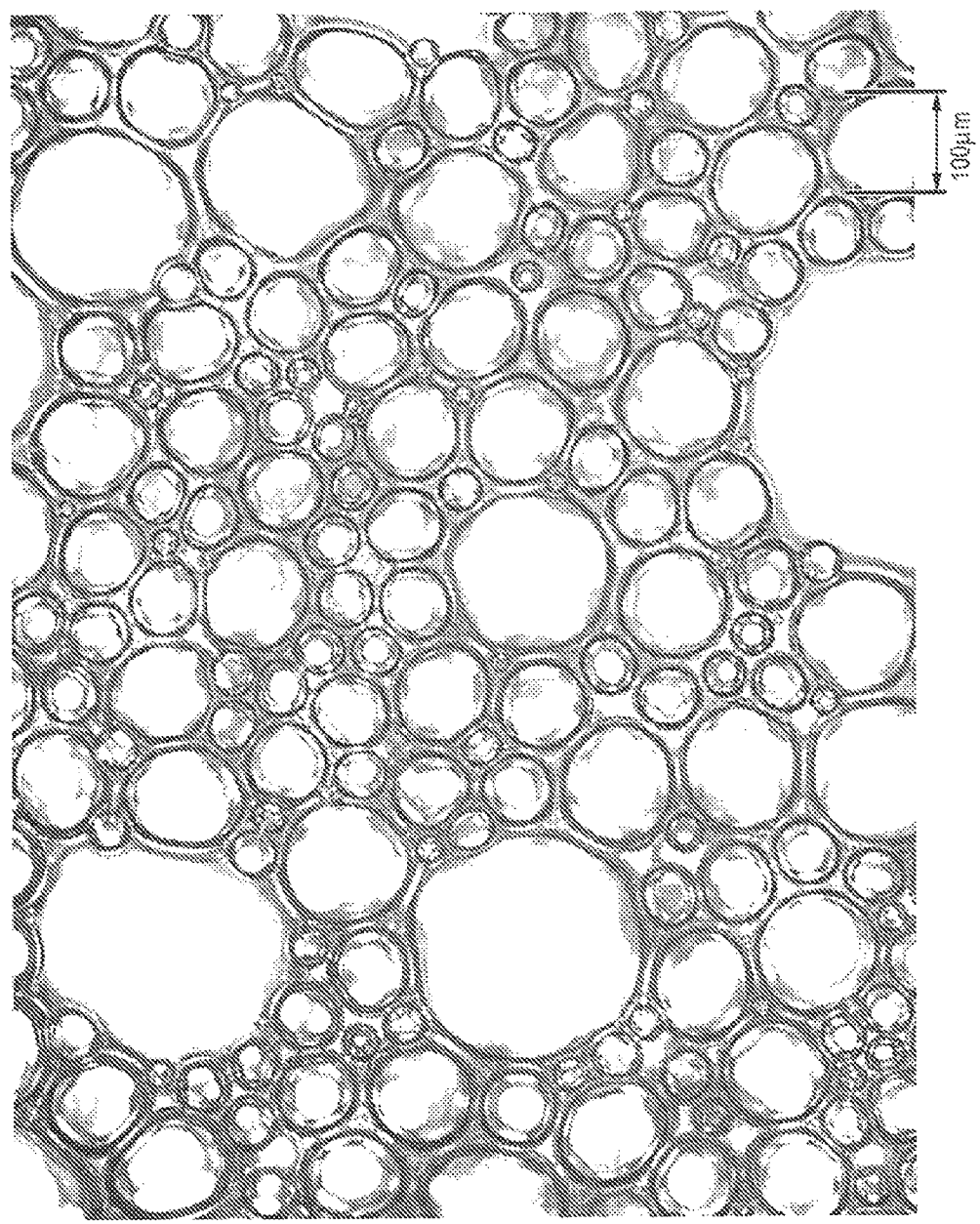
FIG. 9 is a photomicrograph of the foam produced by the prior art Olux® (clobetasol propionate) Foam 0.05% product that was dispensed on to a glass slide, covered and photographed at 100× magnification. A reference 100 µm bar is shown in the lower right corner of each of FIGS. 8 and 9.

The diameter and shape of a dispensed foam of the present invention and that of the Olux® (clobetasol propionate) Foam 0.05% product are not the only areas of difference between the two. Thus, FIG. 8 and FIG. 9 are photomicrographs of dispensed foams from the improved foamable pharmaceutical product of the present invention and the Olux® product, respectively. A small amount of each composition was dispensed on to a microscope slide at ambient laboratory temperature and the resulting foam was covered with a cover slip. The covered slide was then placed in a microscope and after focusing, a photograph was taken. From dispensing to photograph, it is estimated that less than one minute elapsed in each instance.

Examination of the two photos shows that the two foams contain very differently sized bubbles and the diameters of those bubbles are distributed quite differently. Thus, when dispensed as mousse-like foam from the Olux® (clobetasol propionate) Foam 0.05% product as shown in FIG. 9, the average foam bubble diameter size was about 70 μm, with standard deviation of the sample set of 57 μm, and a relative standard deviation (RSD) of about 81%. Measurable bubbles ranged in diameter from 7.3 to 229.5 μm. About 40% of the bubbles had diameters of less than about 40 μm. On the contrary, the average bubble diameter from the sprayed foam of the foamable pharmaceutical product of the invention (FIG. 9) was about 17 μm. The standard deviation was 16 μm and the RSD was about 94%. Measurable bubble diameters ranged from 0.1 to 72.1 μm. About 90% of the bubbles had diameters of less than about 40 μm.

The uniformity of product delivery is improved by the present invention, presumably due to the enhanced uniformity of the foam bubbles. In addition, a foam of the present invention breaks or collapses into its liquid form more quickly than does a foam of the Olux® (clobetasol propionate) Foam 0.05% product, with a greater amount of foam in contact with the relatively warm skin, providing the foam with a greater surface area for contact with the air, and less insulating foam surrounding the skin-contacting layer of bubbles.

A more rapid collapse into a liquid can translate into less irritation of the skin needing treatment that is otherwise subject to rubbing to distribute the foam/liquid. The direct spraying of the foam onto the affected skin area and the larger diameter spray pattern that results also leads to a decreased amount of rubbing on the affected skin because the foam need not be spread as broadly.

Once in its liquid form due to the heat from the skin, the released aliphatic alcohol and corticosteroid active substance penetrate the skin site, leaving a low amount of residue. This route of administration facilitates the ease of specific local application to a greater extent than that provided by the Olux® (clobetasol propionate) Foam 0.05% product, and the composition according to the invention provides a more convenient, controllable and efficient vehicle for delivering a topically active corticosteroid to the skin.

This improved application can facilitate better patient compliance with a prescribed dosing regimen. A composition of the present invention can be used in treating skin diseases that are conventionally treated with corticosteroid active substances. Thus, the composition can be used in the treatment of, inter alia, eczema, infantile eczema, atopic dermatitis, dermatitis herpetiformis, contact dermatitis, seborrhoeic dermatitis, neurodermatitis, psoriasis and intertrigo. A composition is especially useful in the treatment of scalp psoriasis in human subjects.

The present invention is illustrated by the following non-limiting Examples:

EXAMPLE 1

Betamethasone Valerate Formulation

A betamethasone valerate formulation having the following composition was prepared:

| Component | % w/w |
|---|---|
| Betamethasone Valerate | 0.12 |
| Cetyl Alcohol BP | 1.10 |
| Octadecan-1-ol BP | 0.50 |
| Polysorbate 60 BP | 0.40 |
| Ethanol | 57.79 |
| Purified Water | 33.69 |
| Propylene Glycol BP | 2.00 |
| Citric Acid Anhydrous BP | 0.073 |
| Potassium Citrate | 0.027 |
| Butane/Propane | 4.30 |
| | 100.00 |

Cetyl alcohol (HYFATOL™ 1698, Efkay Chemicals Limited, London), octadecan-1-ol (HYFATOL™ 1898, Efkay Chemicals Limited, London), Polysorbate 60 (CRILLET™ 3, Croda Chemicals, North Humberside) and ethanol in the correct proportions were mixed and heated to about 45° C., with continuous stirring until the mix became clear. Betamethasone valerate BP (Roussel Uclaf, Virtolaye, France) was slowly transferred into the mix, again with continuous stirring until the mix became clear. (Alcoholic Phase)

Purified water was separately heated to 45° C. and anhydrous citric acid BP and potassium citrate BP in the above amounts were transferred to the water, with continuous stirring until dissolved.
(Aqueous Phase)

The Alcoholic and Aqueous phases were each filtered through 75 micron screens and the required weights filled into a can (aluminium, epoxy lined) at room temperature. After sealingly attaching a valve assembly without the actuator, the butane/propane propellant (Propellant P70) was added to the mix in the can to the required weight, and an actuator added to the valve.

EXAMPLE 2

Clobetasol Propionate Formulation

A clobetasol propionate formulation having the following composition was prepared as discussed above:

| Component | % w/w |
|---|---|
| Clobetsasol Propionate | 0.050 |
| Cetyl Alcohol BP | 1.14 |
| Octadecan-1-ol BP | 0.51 |
| Polysorbate 60 BP | 0.41 |
| Ethanol | 60.71 |
| Purified Water | 35.29 |
| Propylene Glycol BP | 2.09 |
| Citric Acid Anhydrous BP | 0.08 |
| Potassium Citrate | 0.13 |
| Menthol | 0.05-0.08 |
| Butane/Propane | 4.5-7.50* |
| | 100.00 |

*This propellant (AP-70) contains about 55% propane. Different amounts are used for differently sized containers.

EXAMPLE 3

Spray Pattern Studies

The illustrative formulation of Example 2 was used to conduct several spray pattern studies.

Study 1: Coverage Area

Product was dispensed from the pressurized container onto a solid glass surface at ambient room temperature to evaluate the approximate area covered by similar weights of product. Approximately 2 g of composition was dispensed onto the glass surface and the diameter was measured to the nearest centimeter (cm) at each spray distance (distance of the spray orifice from the glass). The results of this study are shown in the Table below.

| Spray Distance from | After 1 Second of Spray | |
|---|---|---|
| Glass in inches (cm) | Diameter (cm) | Area (cm²) |
| 2 (5.1) | 3 | 7.1 |
| 3 (7.6) | 7 | 38.5 |
| 4 (10.2) | 11 | 95 |

Study 2: Activator Evaluation

Several actuators were evaluated for their quality of dispensing. Several foamable pharmaceutical product containers were filled as similarly as possible and the separate cans of foamable composition were fitted with different actuators. The can was held at approximately a 45° angle at about 2-3 inches above a flat glass surface as above. Each was actuated for about one second.

The actuators had different orifice diameters and different styles of delivery. One delivery profile was called "Aqua" and the other "Concave" by the manufacturer, Precision Valve, Inc. [valve actuator part numbers 21-8121 (0.013" MB Aqua), 21-8122 (0.016" MB Aqua), 21-8123 (0.020" MB Aqua), 21-8141 (0.013" MB Concave), 21-8142 (0.016" MB Concave), and 21-8143 (0.020" MB Concave)]. The "Aqua" version is designed to have a targeted delivery pattern and the "Concave" is designed to have a conical circular delivery pattern.

Three orifice diameters (0.013, 0.016 and 0.020 inches) were studied for each type actuator, with the 0.013 inch diameter Concave actuator providing the best overall features of focused pattern and uniform foam. Wider actuator diameters provided a hollow area in the middle of the spray pattern and the 0.013 inch diameter Aqua actuator provided sporadic pattern.

Study 3: Foam Density and Dispensing Rate

A commercial container of the Olux® (clobetasol propionate) Foam 0.05% product was inverted and dispensed for 5 seconds onto a weigh boat to provide 17.3 g, or a rate of about 3.5 g/second, of foam. A can containing the composition of Example 2 and a preferred 0.013 diameter orifice Concave actuator was sprayed for 5 seconds into a similar weigh boat to provide 4.1 grams of foam, for a spray rate of about 0.82 grams/second.

Initial foam densities were measured by spraying foam into a pre-weighed 10 mL plastic syringe that was at ambient room temperature. The syringe plunger was gently moved to the 5 mL line to express extra foam from the syringe, followed by reweighing the foam-containing beaker. The foam weights were 0.52 grams for the Olux® (clobetasol propionate) Foam 0.05% product and 0.77 grams for the composition of Example 2 dispensed as discussed above. Division of each weight by 5 mL provides densities of about 0.10 and 0.15 grams/mL, respectively. Thus, a contemplated composition provides a foam that is about one and one-half times as dense as that of the Olux® (clobetasol propionate) Foam 0.05% product. Once the foam is dispensed into the syringe, the remainder of the manipulations and measurements for determining density typically take less than about 30 seconds.

Each of the patents, patent applications and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

What is claimed is:

1. A pharmaceutical composition comprising: an effective amount of clobetasol propionate as an active ingredient; a quick-break foaming agent that comprises a C1-C4 aliphatic alcohol, water, a fatty alcohol and a surface active agent; a buffering agent present in an amount sufficient to provide a pH value of about 3.0 to about 6.0; a propellant; and a fragrance; said pharmaceutical composition being disposed in a pressurized container having an aerosol valve assembly, said aerosol valve assembly adapted to dispense a spray upon actuation that forms a quick-breaking foam mousse when applied to a skin surface, and an actuator having a diameter of approximately 0.013 inches at the point of actuation to start and stop dispensation.

2. The pharmaceutical composition of claim 1, wherein the C1-C4 aliphatic alcohol comprises ethanol at a concentration of about 57 to about 62% w/w of the composition.

3. The pharmaceutical composition of claim 1, wherein the water is present at a concentration of about 25 to about 40% w/w of the composition.

4. The pharmaceutical composition of claim 1, wherein the fatty alcohol is present at a concentration of about 0.5 to about 10% w/w of the composition.

5. The pharmaceutical composition of claim 1, wherein the fatty alcohol is a mixture of fatty alcohols and is present at a concentration of about 0.5 to about 10% w/w of the composition.

6. The pharmaceutical composition of claim 1, wherein the fatty alcohol comprises cetyl alcohol.

7. The pharmaceutical composition of claim 1, wherein the fatty alcohol comprises a stearyl alcohol.

8. The pharmaceutical composition of claim 1, wherein the surface active agent is a nonionic surface active agent at a pH of between about 5 and about 9 having an HLB value of about 13 to about 17.

9. The pharmaceutical composition of claim 1, wherein the surface active agent is a nonionic surface active agent at a pH of between about 5 and 9, having an HLB value of about 13 to about 17, and is present at a concentration of about 0.3 to about 5% w/w of the composition.

10. The pharmaceutical composition of claim 1, wherein the surface active agent is selected from the group consisting of an ethoxylated sorbitan, palmitate C12-C18 ester, or laurate C12-C18 ester, a nonyl phenol ethoxylate, and ethoxylated paraffinic alcohol; and is present at a concentration of about 0.3 to about 5% w/w of the composition.

11. The pharmaceutical composition of claim 1, wherein the propellant used is selected from the group consisting of propane, butane, dichlorodifluoromethane, dichlorotetrafluoroethane, octafluoro cyclobutane and their mixtures.

12. The pharmaceutical composition of claim 1, wherein the fragrance is present at a concentration of about 0.02% to about 0.1% w/w of the composition.

13. The pharmaceutical composition of claim 1, further comprising a humectant at a concentration of about 0.1 to about 10% w/w of the composition.

14. A pharmaceutical composition comprising: an effective amount of clobetasol propionate as an active ingredient; a quick-break foaming agent that comprises a straight or branched chain C1-C4 aliphatic alcohol, water, a fatty alcohol and a surface active agent; a buffering agent present in an amount sufficient to provide a pH value of about 3.0 to about 6.0; and a propellant; said foamable pharmaceutical composition being disposed in a pressurized container, said container having an actuator having a diameter of approximately 0.013 inches at the point of actuation to start and stop dispensation and an aerosol valve assembly that when actuated sprays a foam mousse having an average foam bubble diameter of about 5 to about 40 µm, with at least 90 percent of the bubbles having a diameter of less than 40 µm, such that it forms a quick-breaking foam mousse when applied to a skin surface.

15. The pharmaceutical composition of claim 14, wherein the propellant provides an internal pressure in the pressurized container of about 40 to about 80 psi when the pressurized container is sealed.

16. The pharmaceutical composition of claim 14, wherein the container has an aerosol valve assembly that when actuated dispenses the foam mousse spray at a rate of about 0.3 to about 2 g/sec.

17. The pharmaceutical composition of claim 14, wherein the foam mousse spray has an initial density of about 0.12 to about 0.25 g/mL when sprayed at a distance of about 5 to about 10 cm.

18. The pharmaceutical composition of claim 14, wherein the average bubble diameter is about 10 to about 25 µm.

* * * * *